(12) United States Patent
Turner et al.

(10) Patent No.: US 9,050,431 B2
(45) Date of Patent: Jun. 9, 2015

(54) DEVICE FOR DISPENSING A MEDIUM

(75) Inventors: Jeffrey Turner, San Clemente, CA (US);
Brian Hack, Cambridge, MA (US);
Richard L. Miller, Needham, MA (US)

(73) Assignee: Jeffrey Turner, San Clemente, CA (US)

( * ) Notice: Subject to any disclaimer, the term of this patent is extended or adjusted under 35 U.S.C. 154(b) by 1205 days.

(21) Appl. No.: 12/906,832

(22) Filed: Oct. 18, 2010

(65) Prior Publication Data

US 2012/0090628 A1    Apr. 19, 2012

(51) Int. Cl.
*A24F 47/00* (2006.01)
*A61M 15/06* (2006.01)
*A61M 15/00* (2006.01)
*A61M 15/08* (2006.01)

(52) U.S. Cl.
CPC ............. *A61M 15/06* (2013.01); *A61M 15/009* (2013.01); *A61M 15/08* (2013.01)

(58) Field of Classification Search
CPC .... A24F 47/00; A24F 47/002; A61M 15/009; A61M 15/06; A61M 15/08
USPC .......................... 131/270–273, 360, 194, 329
See application file for complete search history.

(56) References Cited

U.S. PATENT DOCUMENTS

| | | | |
|---|---|---|---|
| 580,736 | A | 4/1897 | Smith |
| 1,459,478 | A | 6/1923 | Page |
| 1,789,921 | A | 1/1931 | Adam |
| 2,064,314 | A | 12/1936 | Morin |
| 2,142,353 | A | 1/1939 | Griffith |
| 2,579,280 | A | 12/1951 | Trumbour et al. |
| 2,613,527 | A | 10/1952 | Harris |
| 2,651,303 | A | 9/1953 | Johnson et al. |
| 2,681,560 | A | 6/1954 | Shuttleworth et al. |
| 2,721,551 | A | 10/1955 | Lobl |
| 3,012,694 | A | 12/1961 | Johnston |
| 3,200,819 | A | 8/1965 | Gilbert |
| 3,320,953 | A | 5/1967 | Rindner |
| 3,404,692 | A | 10/1968 | Lampert |
| 3,424,123 | A | 1/1969 | Giffard |
| 3,425,414 | A | 2/1969 | La Roche |

(Continued)

FOREIGN PATENT DOCUMENTS

| | | |
|---|---|---|
| DE | 3 718 910 A1 | 12/1988 |
| EP | 0 111 163 A2 | 6/1984 |

(Continued)

OTHER PUBLICATIONS

ECigarettes USA, Inc., "Product Information", PO Box 152877, Cape Coral, Florida 33915, USA, pp. 1-2, email: info@ECigarettesUSA.com; http://www.ecigarettesusa.com /info.cfm, printed May 8, 2002.

(Continued)

*Primary Examiner* — Richard Crispino
*Assistant Examiner* — Dionne Walls Mayes
(74) *Attorney, Agent, or Firm* — Wolf, Greenfield & Sacks, P.C.

(57) ABSTRACT

A device for dispensing a medium is disclosed. The device comprises an elongated body including a chamber for containing a medium and an outlet through which the medium exits the device into an oral or nasal opening. A dispensing system selectively places the chamber and the outlet in communication, causing medium to flow out of the device.

24 Claims, 5 Drawing Sheets

(56) References Cited

U.S. PATENT DOCUMENTS

| | | | |
|---|---|---|---|
| 3,482,580 A | 12/1969 | Hollabaugh |
| 3,521,643 A | 7/1970 | Toth |
| 3,631,856 A | 1/1972 | Taylor |
| 3,721,240 A | 3/1973 | Tamburri |
| D226,824 S | 5/1973 | Staub |
| 3,789,840 A | 2/1974 | Rosenblatt |
| 3,886,953 A | 6/1975 | Pope |
| D244,517 S | 5/1977 | Spencer |
| 4,171,000 A | 10/1979 | Uhle |
| 4,393,884 A | 7/1983 | Jacobs |
| 4,429,703 A | 2/1984 | Haber |
| 4,730,628 A | 3/1988 | Townsend et al. |
| 4,735,217 A | 4/1988 | Gerth et al. |
| 4,756,318 A | 7/1988 | Clearman et al. |
| 4,759,380 A | 7/1988 | Norman et al. |
| 4,765,348 A | 8/1988 | Honeycutt |
| 4,774,971 A | 10/1988 | Vieten |
| 4,793,365 A | 12/1988 | Sensabaugh, Jr. et al. |
| 4,807,648 A | 2/1989 | Breckwoldt |
| 4,854,332 A | 8/1989 | Hanakura |
| 4,877,041 A | 10/1989 | Barnhouse |
| 4,893,639 A | 1/1990 | White |
| 4,924,888 A | 5/1990 | Perfetti et al. |
| 4,942,888 A | 7/1990 | Montoya et al. |
| 4,945,929 A | 8/1990 | Egilmex |
| 4,945,931 A | 8/1990 | Gori |
| 4,984,588 A | 1/1991 | Stewart, Jr. |
| 4,993,436 A | 2/1991 | Bloom, Jr. |
| 4,995,407 A | 2/1991 | Kossiakoff et al. |
| 5,042,510 A | 8/1991 | Curtiss et al. |
| 5,101,839 A | 4/1992 | Jakob et al. |
| 5,105,831 A | 4/1992 | Banerjee et al. |
| 5,105,836 A | 4/1992 | Gentry et al. |
| 5,240,153 A * | 8/1993 | Tubaki et al. ................ 222/385 |
| 5,284,163 A | 2/1994 | Knudsen et al. |
| 5,400,808 A | 3/1995 | Turner et al. |
| 5,415,186 A | 5/1995 | Casey, III et al. |
| 5,499,636 A | 3/1996 | Baggett, Jr. et al. |
| 5,501,236 A | 3/1996 | Hill et al. |
| 5,509,581 A | 4/1996 | Parsons |
| 5,535,735 A | 7/1996 | McPherson |
| 5,598,868 A | 2/1997 | Jakob et al. |
| 5,611,360 A | 3/1997 | Tang |
| D402,753 S | 12/1998 | White |
| 5,865,185 A | 2/1999 | Collins et al. |
| 5,906,811 A | 5/1999 | Hersh |
| 5,992,421 A | 11/1999 | Bae |
| 6,041,789 A | 3/2000 | Bankert et al. |
| 6,041,790 A | 3/2000 | Smith et al. |
| 6,098,632 A | 8/2000 | Turner et al. |
| 6,206,008 B1 | 3/2001 | Matteau et al. |
| 6,216,705 B1 | 4/2001 | Ossepian |
| 6,538,010 B1 | 3/2003 | Carroll |
| 6,543,653 B2 * | 4/2003 | Lamboux ................ 222/321.8 |
| 6,725,867 B2 | 4/2004 | Peterson et al. |
| 6,845,777 B2 | 1/2005 | Pera |
| 6,854,470 B1 | 2/2005 | Pu |
| 7,013,888 B2 | 3/2006 | Hughes et al. |
| D584,409 S | 1/2009 | Miller et al. |
| D590,990 S | 4/2009 | Hon |
| D624,238 S | 9/2010 | Turner |
| D642,330 S | 7/2011 | Turner |
| 8,251,075 B2 * | 8/2012 | Breese et al. ................ 132/299 |
| 2002/0059939 A1 | 5/2002 | Fox |
| 2002/0179101 A1 | 12/2002 | Chavez |
| 2004/0261804 A1 | 12/2004 | Mitchell |
| 2005/0016550 A1 | 1/2005 | Katase |
| 2006/0018840 A1 | 1/2006 | Lechuga-Ballesteros et al. |
| 2006/0237024 A1 | 10/2006 | Reich et al. |
| 2006/0254604 A1 | 11/2006 | Martinez Fernandez |
| 2008/0177246 A1 * | 7/2008 | Sullivan et al. ................ 604/520 |
| 2008/0271744 A1 | 11/2008 | Danforth |
| 2009/0188490 A1 | 7/2009 | Han |
| 2009/0258326 A1 | 10/2009 | Al-Sulaiman et al. |
| 2011/0290268 A1 * | 12/2011 | Schennum ................ 131/330 |

FOREIGN PATENT DOCUMENTS

| | | |
|---|---|---|
| EP | 0 824 927 A2 | 2/1998 |
| FR | 2 293 221 A1 | 7/1976 |
| FR | 2 654 002 A1 | 11/1989 |
| GB | 16627 | 0/1910 |
| WO | WO 87/05813 A1 | 10/1987 |
| WO | WO8809680 * | 12/1988 |
| WO | WO 93/25258 A1 | 12/1993 |
| WO | WO 01/52927 A1 | 7/2001 |
| WO | WO 03/000327 A1 | 1/2003 |
| WO | WO 2009/001078 A2 | 12/2008 |
| WO | WO 2009/001082 A1 | 12/2008 |

OTHER PUBLICATIONS

Consumer Medicine Information, "*How to use the Inhaler*", pp. 1-2, http://www.medsafe.govt.nz/consumers/cmi/n/NicoretteInh10mg.htm, printed May 11, 2009.

* cited by examiner

DEVICE FOR DISPENSING A MEDIUM

BACKGROUND

Smoking is a national and global epidemic. Tobacco companies manufacture five and a half trillion cigarettes a year. That is nearly 1,000 cigarettes for every man, woman, and child on the planet. Global consumption of cigarettes has been rising steadily since their introduction at the beginning of the 20$^{th}$ century. While consumption is leveling off and even decreasing in some countries, worldwide more people are smoking, and smokers are smoking more cigarettes. The number of smokers will increase mainly due to the expansion of the world's population. By 2030 there will be at least another 2 billion people in the world (Census Bureau). Even if prevalence rates fall, the absolute number of smokers will increase.

According to the American Cancer Society, about 70% of smokers want to quit smoking, and 35% attempt to quit every year. Unfortunately, fewer than 5% of those smokers attempting to quit succeed. The number one recommended therapy for smokers desiring to quit is Nicotine Replacement Therapy (also known as NRT). The most common delivery methods for nicotine are a pill/lozenge, a patch, or a gum. However, these therapies do nothing to address the behavioral addiction of smoking.

The average smoker smokes 15 cigarettes a day and takes an average of 10 "drags" or inhalations per cigarette. Thus the behavioral addiction is reinforced in a smoker's body 150 times per day every day for as many years as the smoker has had the habit. The hand-to-mouth tactile experience of smoking, oral fixation, deep inhalation, sensation of smoke hitting the back of the throat, and the exhalation are all behavioral traits that smokers are addicted to experiencing during the act of smoking. Further, the ritual of smoking is associated with everyday events: after a meal, at coffee breaks, driving or riding in a car, stressful events, etc. While the dopamine "high" that nicotine provides is addicting, a therapy for addressing the behavioral addiction is also needed.

SUMMARY

The inventor has recognized and appreciated a need for a therapy for addressing the behavioral addiction of smoking. More generally, the inventor has recognized the advantages of a device capable of delivering a medium, such as an inhalable, ingestible or absorbable medium, that is useful in such a therapy. Such a device is capable of being used for any number of different applications besides smoking cessation therapy.

In one exemplary embodiment, a device for dispensing a medium includes an elongated body with a chamber for containing a medium and an outlet configured for delivering the medium to an oral or nasal opening. The device also includes a dispensing system for selectively placing the chamber in communication with the outlet. The dispensing system includes a button that is selectively moveable in a direction transverse to the elongated body to actuate dispensing of the medium from the chamber and through the outlet.

In another embodiment, a device for dispensing a medium includes an elongated body having a chamber for containing a medium and an outlet configured for delivering the medium to an oral or nasal opening. The device also includes a dispensing system for placing the chamber in communication with the outlet, the dispensing system being selectively actuable by a substantially constant force button.

In a further embodiment, a device for dispensing a medium includes an elongated chamber section for containing a medium and an elongated dispensing section. The dispensing section includes an outlet configured for delivering the medium through an oral or nasal opening, a conduit in communication with the outlet, a valve, a button moveable in a direction transverse to the dispensing section, and a linkage operatively associated with the valve and the button. The elongated chamber section and the elongated dispensing section are releasably attachable in end-to-end relation to form an elongated body. The valve is openable in response to movement of the button in the transverse direction, causing medium in the chamber to flow through the valve, along the conduit and out of the device via the outlet.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

The foregoing and other aspects, embodiments, and features of the present teachings can be more fully understood from the following description in conjunction with the accompanying drawings.

BRIEF DESCRIPTION OF THE DRAWINGS

The accompanying drawings are not intended to be drawn to scale. For purposes of clarity, not every component may be labeled in every drawing. In the drawings.

DETAILED DESCRIPTION

Figure 1:
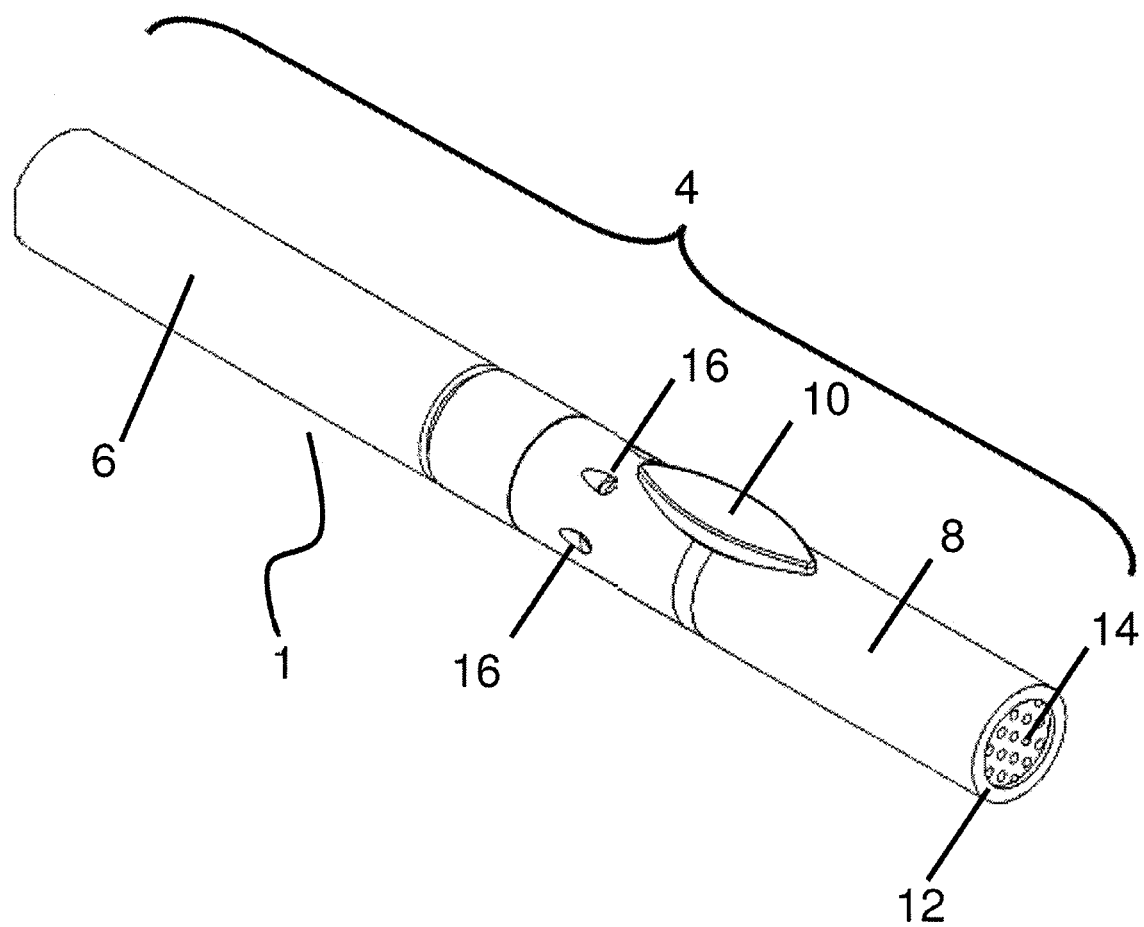
FIG. 1 shows a perspective view of the device.
Figure 2:
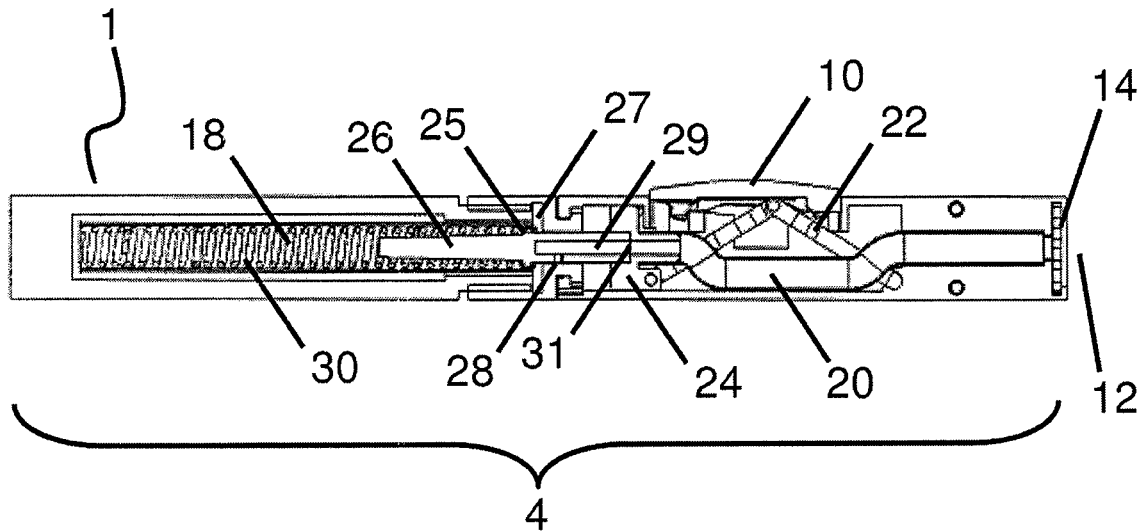
FIG. 2 shows a sectional view of the device in a closed position.
Figure 3:
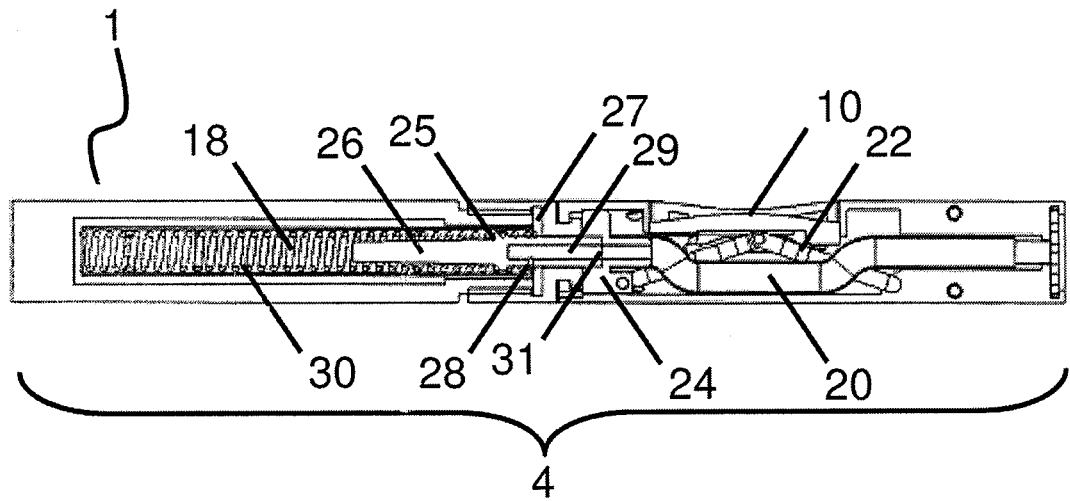
FIG. 3 shows a sectional view of the device in an open position.
Figure 4:
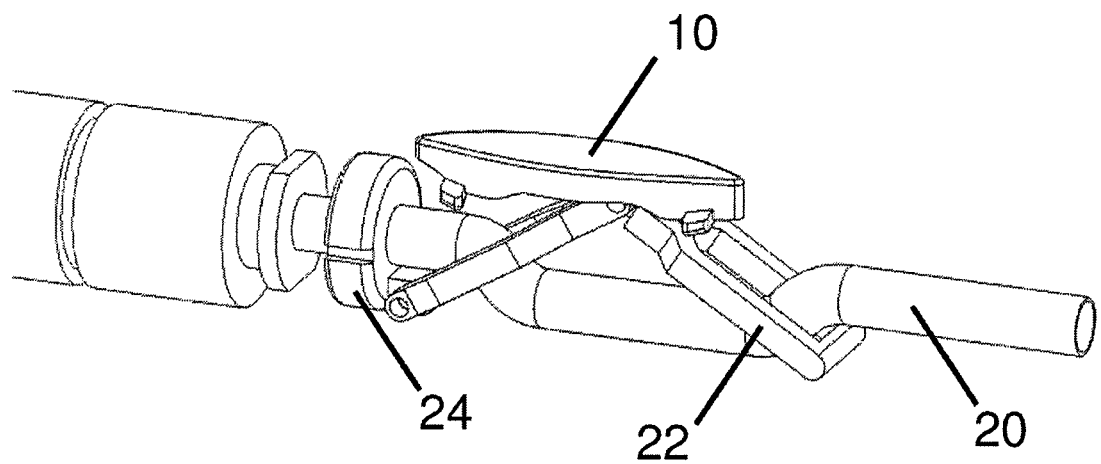
FIG. 4 shows a perspective view of the actuator button, linkage, and conduit in a closed position.
Figure 5:
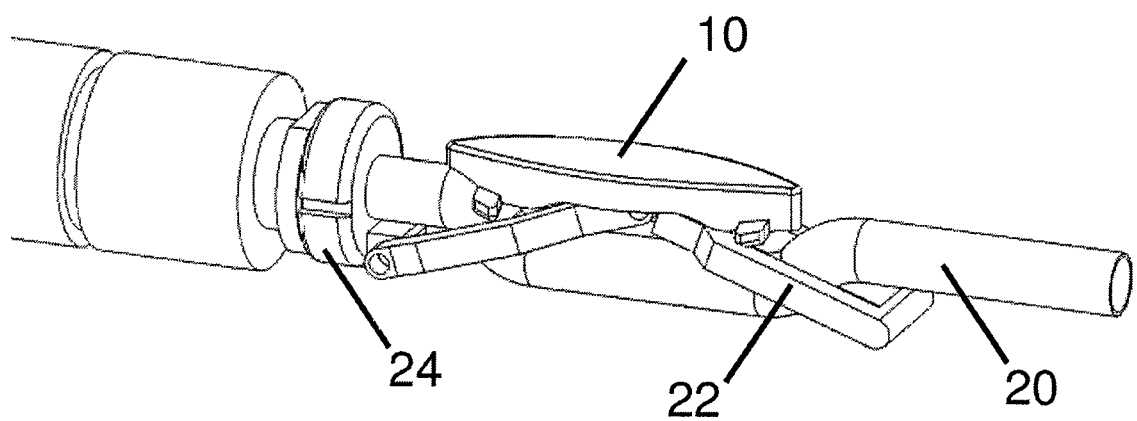
FIG. 5 shows a perspective view of the actuator button, linkage, and conduit in an open position.
Figure 6:
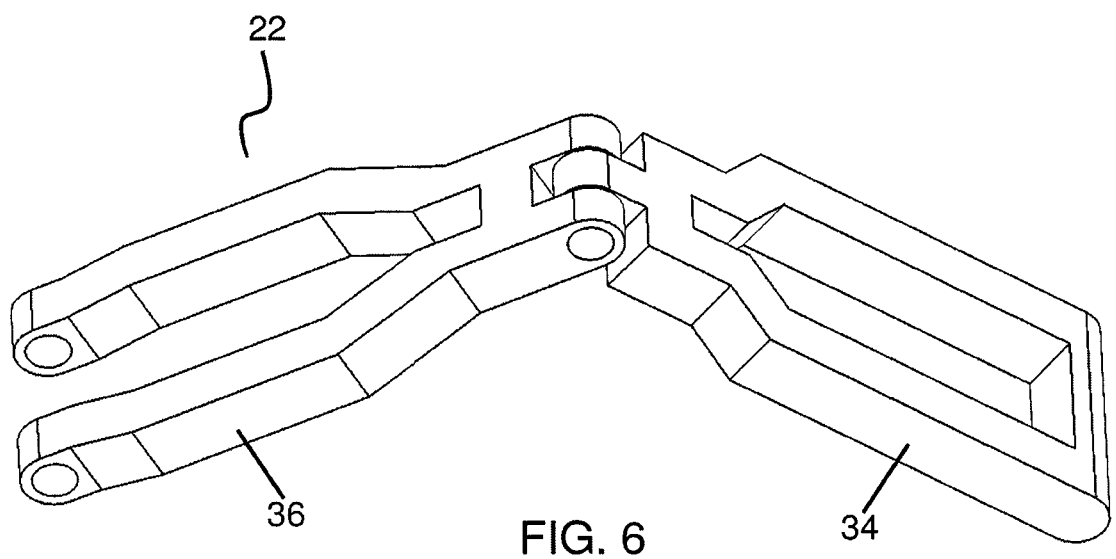
FIG. 6 shows a view of the linkage.
Figure 7:
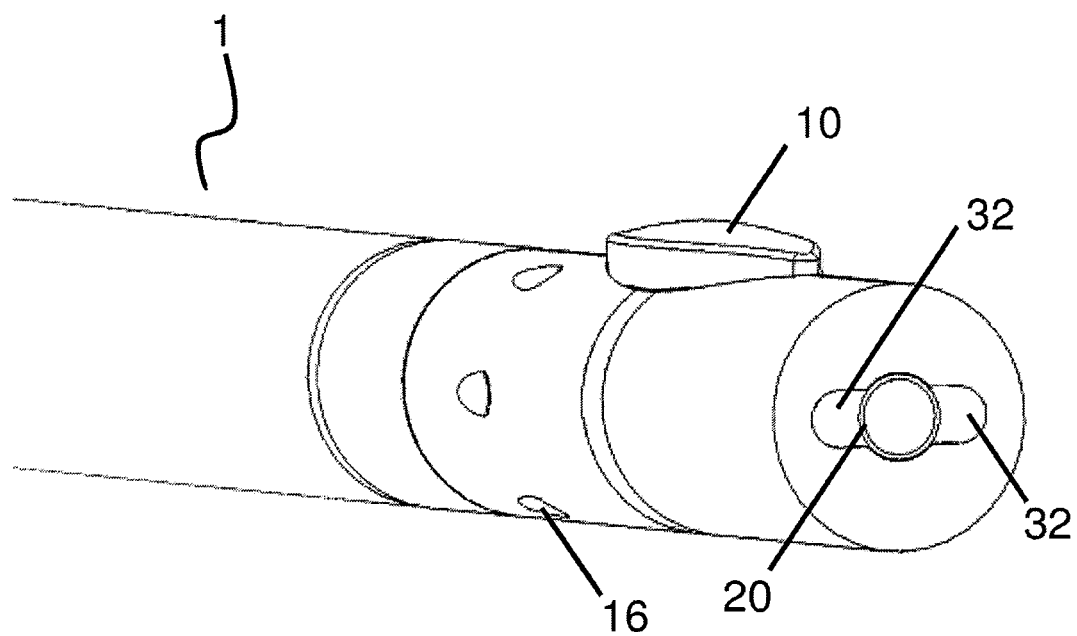
FIG. 7 shows a sectioned perspective view of a mouthpiece end of the device.
Figure 8:
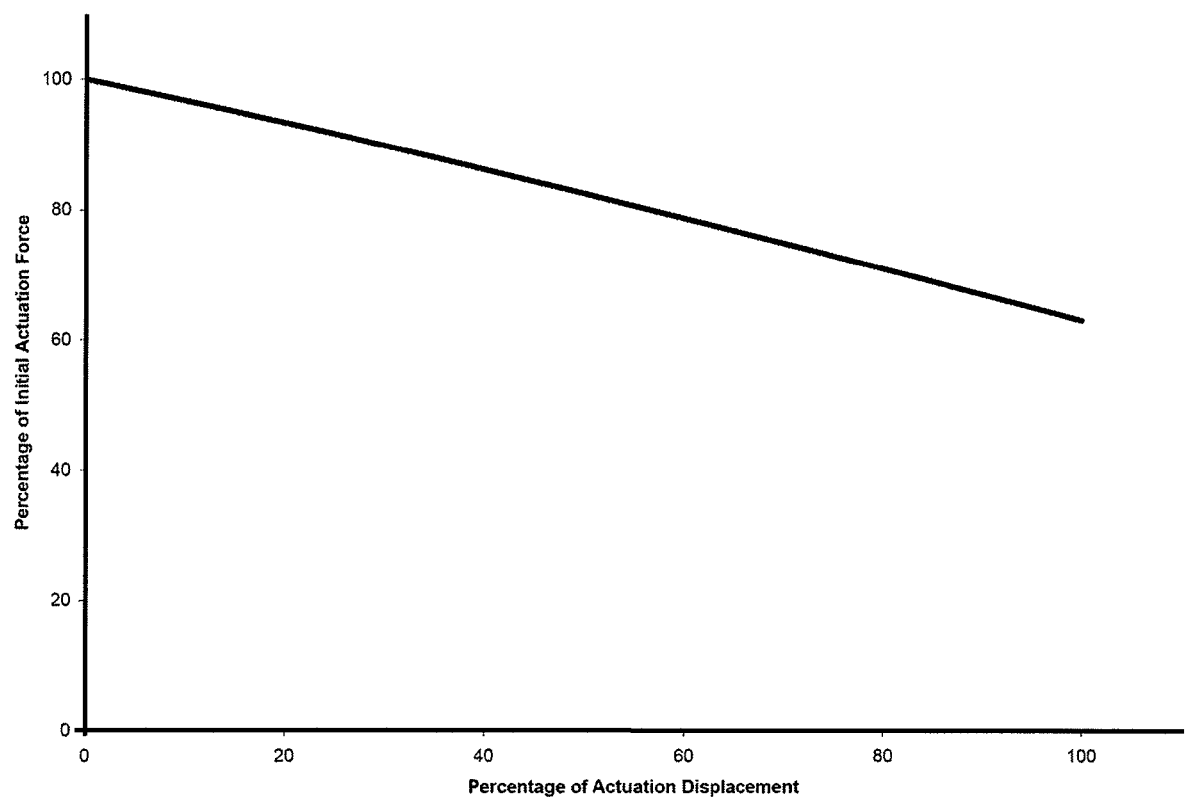
FIG. 8 shows a graph of actuation force versus actuation displacement.

It should be understood that aspects of the invention are described herein with reference to the figures, which show illustrative embodiments in accordance with aspects of the invention. The illustrative embodiments described herein are not necessarily intended to show all aspects of the invention, but rather are used to describe a few illustrative embodiments. Thus, aspects of the invention are not intended to be construed narrowly in view of the illustrative embodiments. It should be appreciated, then, that the various concepts and embodiments introduced above and those discussed in greater detail below may be implemented in any of numerous ways, as the disclosed concepts and embodiments are not limited to any particular manner of implementation. In addition, it should be understood that aspects of the invention may be used alone or in any suitable combination with other aspects of the invention.

A device for dispensing a medium, such as an inhalable, ingestible or absorbable medium, includes an elongated body having a chamber for containing the medium and a dispensing system for selectively delivering the medium out of an outlet and through a nasal or oral opening. The dispensing system may include a valve, an actuator for the valve, the outlet, and a conduit that allows communication between the valve and the outlet. The actuator may include a linkage operatively connected to the valve and a button that a user may selectively manipulate to open the valve releasing the medium. The button may be located along the length of the body between the opposed ends. The button, in certain embodiments, is positioned closer to one end than the other of the elongated body (e.g., closer to a mouthpiece or nasalpiece end) at a location comparable to placement of the index or middle fingers if one were holding the elongated body like a cigarette. Other locations of the button, however, are contemplated. While in a closed position, the button may project from the surface of the body, be flush mounted with the surface of the body, or be depressed below the surface of the body. The button is arranged to be pressed, or otherwise actuated, in a direction transversely to the elongated body to open the valve. Other directional movements of the button to dispense the medium are contemplated as should be apparent to one of skill in the art. The dispensing system may be configured so that a relatively constant force moves the button from the closed position to the open position, actuating discharge of the medium.

The elongated body may have a tubular shape, similar in size and length to a conventional cigarette so that it may be held between the index or middle fingers like a cigarette providing a tactile experience like smoking, although other shapes and sizes of an elongated body are contemplated as should be apparent to one of skill in the art. The elongated body may be a single, unitary structure, or may include two or more separable and, optionally, reconnectable body sections. One or both of such reconnectable body sections may be reusable. At least one of the medium chamber and the dispensing system may reside in separate body sections or may include aspects that span between different body sections. Either of the medium chamber section or the dispensing system section may be reusable; for example, and without limitation, when a medium chamber section is spent, it may be removed and replaced by a fresh medium section. Rather than discarding the spent medium section, it may be refilled and then reconnected to the dispensing system section. The dispensing system may provide a continuous, metered, pulsatile or other dispensing discharge of the medium as should be apparent to one of skill in the art. A dispersing feature may be provided in the device to influence the properties of the medium that is discharged. For example, and without limitation, the dispersing feature may break up the medium into finer constituents or change the flow characteristics or pattern of the medium. Arrangements may be provided in the device to mix air with the medium prior to exiting the body. The medium may include nicotine, stimulant, medication, antioxidant, breath-freshener, mixtures of any of the foregoing, or any other desirable medium, and may further include a propellant. The medium is not limited to a particular composition, nor to a form or size of the medium. The medium may be formulated for inhalation, ingestion, absorption or other type of administration as should be apparent to one of skill in the art, and the location of target effect of the medium (e.g., oral cavity, nasal cavity, throat, lungs, stomach) is not necessarily a limitation of the invention. Further, other forms of medium that may be administered to a person are contemplated as should be apparent to one of skill in the art. The chamber may include two or more chambers containing the same or different mediums. The latter arrangement allowing different mediums to be mixed together prior to administration to the user, or for the user to select amongst different mediums, or combinations of mediums, to dispense.

The device 1 for dispensing a medium illustrated in the figures includes an elongated body 4 with a chamber 18 for containing a medium and a dispensing system for selectively dispensing the medium from the chamber 18 through the elongated body 4 to an outlet 12 at an end of the device 1 that is configured for insertion through an oral or nasal opening. As illustrated, the outlet 12 may include a mouthpiece located at an end face of the elongated body 4, although other locations of an outlet 12 are contemplated as should be apparent to one of skill in the art. The dispensing system includes a button 10 that projects from the surface of the elongated body 4 and is configured for movement in a transverse direction towards the elongated body 4 to actuate the dispensing system as described in further detail below. The button 10 is located closer to the outlet end than the opposite end of the elongated body 4, preferably in a position comparable to the location's of the index and/or middle finger if the elongated body 4 is held in the manner of a cigarette. Although the button 10 has an oblong, football-like shape, so as to fit within the confines of the elongated body when depressed, other button shapes may be employed as should be apparent to one of skill in the art.

The chamber 18 may be in the shape of a cylinder, as illustrated, and includes a closed end wall, a side wall and an open end that may be fitted with a valve stem seal 27. The dispensing system includes a valve stem 26 that is moveable in sealing contact through the seal 27. The valve stem 26 is moveable between a first position where an opening 28 to a lumen 29 in the valve stem 26 is not in communication with the chamber 18 and a second position where the lumen opening 28 is in communication with the chamber 18. As shown, the lumen opening 28 is blocked by the seal 27, or is positioned rearward (external) of the seal 27, in the first position, but is forward (or internal) of the seal 27 in the second position. In such a second position, the medium flows from the chamber 18, through the opening 28 and down the valve stem lumen 29. In contrast, in the first position, communication between the valve stem lumen 29 and the chamber 18 is prevented. The valve stem lumen 29 may extend only partially along the length of the valve stem 26, as illustrated, although a longer or shorter lumen may be employed as should be apparent to one of skill in the art. The portion of the valve stem 26 located within the chamber may include a shoulder 25 that is operatively connected with a spring 30 positioned in the chamber 18, biasing the valve stem 26 into the second position. Further, a length of the valve stem 26 located within the chamber 18 may be selected to facilitate stability of the valve stem 26 in the medium environment and during dispensing of the medium. Other valve arrangements may be employed as should be apparent to one of skill in the art.

The button 10 is mounted in an opening through the elongated body 4, which may include structure for guiding movement of the button 10 as it is depressed transversely into the elongated body 4. The button 10 is operatively connected by a linkage 22 to the valve stem 26. The linkage 22 translates transverse movement of the button 10 relative to the axis of the elongated body 4 into axial movement that advances the valve stem 26 into the chamber 18. The linkage 22 may be connected directly to the valve stem 26, or indirectly such as via an actuator slide 24 as shown. In either case, the valve stem 26 moves towards and away from the chamber 18 in response to movement of the linkage 22. Various linkage arrangements may be employed to translate the transverse movement of the actuator button to axial movement of the valve stem 26, as should be apparent to one of skill in the art. Representative is a crank and slider linkage including a fixed pivot for anchoring the linkage 22 and a moving pivot for translating the valve stem 26 into and out of the chamber 18. The head of a first link 34 is pivotally connected to the tail of the second link 36. The head of the second link 36 is pivotally connected to the valve stem 26, in this case indirectly through the actuator slide, and is the axially moving pivot of the crank and slide linkage. The tail of the first link 34 is fixed to the elongated body 4, allowing pivoting but constraining axial movement. The illustrated linkage is, essentially, a pair of crank and slider linkages that are located, respectively, on opposite sides of the axis of the elongated body and integrated together. With respect to the first link 34, a cross arm extends between the tail of the link pairs. The cross arm is fixed in a recessed mount formed in the elongated body. The respective heads of the first links converge inwardly to form a pivot post which is received within a clevis formed by the inwardly converging aspects of the respective tails of the second links. A pin extends through holes in the clevis and pivot post connecting the first and second link pairs. The respective heads of the second links are spaced apart and each include a hole for receiving a pin projecting away from the actuator slide. As should be apparent to one of skill in the art, the location of the pivot post and clevis could be switched between the first and second links and, similarly, the location of the pin and holes between the actuator slide and second links could be reversed.

The junction of the first and second links, 34 and 36, is configured for slidable movement relative to the underside of button 10. The link junction may freely move against the underside of the button or, preferably, a guide may be provided in the bottom of the button. For example, and without limitation, a pair of spaced ribs may extend beneath the button providing a channel in which the link junction, defined by the yoke in the illustrated embodiment, may axially slide. A pair of spaced cross-arms may act as stops of axial movement of the link junction. Other arrangements for guiding axial movement of the link junction relative to the button are contemplated as should be appreciated by one of skill in the art.

A conduit 20 extends between an outlet of the valve stem lumen 31 and the outlet 12 (e.g., mouthpiece) of the elongated body 4, providing a pathway for the medium to exit the device 1. The conduit 20 may be a tube, and in the illustrated embodiment is connected to the actuator slide 24 which, in turn, is connected to the valve stem 26. In this embodiment, the actuator slide 24 includes an opening that receives an end of the conduit tube 20 and an end of the valve stem 26, placing the two flow lines in communication. As shown, the tube may be arranged to move towards and away from the chamber 18 in concert with the actuator slide 24. In other embodiments, the tube may be fixed in position relative to the chamber 18 for example where the outlet end of the valve stem 31 is telescopingly arranged with the conduit tube 20. Alternatively, the conduit 20 could be a duct formed in the elongated body that extends from the outlet of the valve stem 31 to the mouthpiece or nasalpiece of the elongated body. A further embodiment includes a combination of duct and tube running from the area of the valve stem 26 to the outlet 12 of the device. Alternatively, the valve stem 26 could extend completely from the chamber 18 to the outlet 12 of the elongated body 4 with the extension of the valve stem 26 constituting a conduit. A relief may be formed in the elongated body to support the conduit tube, particularly at outlet portion of the device.

As the conduit tube 20 lies in the direction of movement of the actuator, specifically the path of the linkage 22 and potentially of the button 10, both the linkage 22 and the conduit tube 20 may be configured to limit interference therebetween. As illustrated, for example, the lengthwise arms of the links 34 and 36 are thin and spaced from its mirror image counterpart, providing an opening through which the conduit tube 20 extends. Additionally, the conduit tube 20 may be contoured to avoid blocking the path of the links 34 and 36 as they descend into the elongated body in response to transverse actuation of the button 10. For example, and without limitation, the conduit tube 20 may have a non-linear section, such as a deflection, to accommodate movement of the linkage 22. In the illustrated approach, the conduit tube 20 includes a U-shaped bump out that opens towards the path of transverse movement of the link junction and button 10. The bump out may be supported by the floor of the interior of the elongated body as shown, although such an arrangement is not necessarily a feature of the invention. Other designs for optimizing the range of motion of the linkage 22 within the set confines of the elongated body 4 are contemplated as should be apparent to one of skill in the art.

The device may be arranged to automatically close the valve and return the button 10 to the starting or closed position. As shown, for example, the chamber 18 may include a spring 30 that biases against the valve stem 26, for example against shoulder 25 as shown, urging the stem and ultimately the linkage and button operatively associated therewith back to the starting or closed position upon release of the actuating force. In another embodiment, the linkage 22 or button 10 could be biased to urge these components back to the starting or closed position. Other arrangements for returning the dispensing system to the starting or closed position are contemplated as should be apparent to one of skill in the art.

The medium dispensing device may be arranged to supplement the flow of the medium through the elongated body. For example, and without limitation, an air bypass system may be configured in the device which may include one or more vents 16 for drawing ambient air into and through the device. The vents 16 may open into channels 32 that extend through the elongated body and end at or near the outlet of the device. As shown, the channels 32 may exit through the end face of the device on opposite sides of the conduit tube 20. Other outlet configurations of the channels 32 are contemplated as should be apparent to one of skill in the art. Alternatively, the vents 16 and/or channels 32 leading from the vents 16 may connect with the conduit 20, so that the supplemental airflow joins the medium as it courses down the conduit 20 towards the device outlet. In a still further embodiment, the vents 16 may open into the interior of the elongated body 4 containing the dispensing system. Channels 32 provided at a downstream end of the dispensing system, such as in the area of the mouthpiece or nasalpiece surrounding the conduit tube 20, provide a pathway for the bypass air to flow out of the device. In certain embodiments, the dimensions and arrangement of the bypass system are configured so that the flow rate and/or volume of airflow emulates, together with the medium, the airflow through a cigarette. The device may be configured so that bypass air is drawn through vents into the device by a venturi effect of the medium flowing through the conduit, eliminating the need for the user to inhale to get the bypass air to flow.

The device may further include one or more features for dispersing the medium as it is dispensed to a user, or otherwise influencing the flow characteristics or pattern of the exiting medium. As illustrated, a dispersion screen 14 may be located at the mouthpiece or nasalpiece, or elsewhere in the device. The dispersion screen 14 may be in the form of a mesh, foam, or any other appropriate material or construction. The dispersion screen may be treated or coated to enhance one or more dispersion properties. An annular groove or other attachment feature may be provided in the mouthpiece/nasalpiece or other elongated body location to mount or otherwise secure the dispersion feature. Alternatively, or in addition to the dispersion screen, the outlet of the conduit and/or of the bypass system may be configured to affect the dispersion characteristics of the dispensed medium. Further, an orifice may be located anywhere along the conduit path to influence dispersion properties of the medium.

As observed earlier, the elongated body 4 may be provided as a unitary structure or as separate body sections. As illustrated, the body sections may be divided between a chamber section 6 and a dispensing section 8. Here, the chamber section 6 includes a neck that is engageably received within a mouth of the dispensing section 8. The connection between the neck and mouth may be threadable, snap-fitting, bayonet-coupling, or other customary arrangement and may be releasable or permanent as should be apparent to one of skill in the art. The chamber section 6 may include a peel away or pierceable lid, or a plug, that covers the valve stem 26 opening to prevent inadvertent emptying of the chamber. The lid or plug may be removed when the chamber section and dispensing section are assembled, or the valve stem 26 may pierce or otherwise extend through the covering when the two sections are united. The chamber section 6 may include a closed orifice that may be opened to replenish the medium.

In one particular embodiment, the dispensing system is configured so that the button is actuable by a substantially constant or near constant force. Depending on the designed mechanical advantage of the linkage and the stiffness of the included spring, it is possible that the force required to actuate the button could slightly decrease or increase during the travel of the button from the closed to the open position. A representative actuation behavior is illustrated in FIG. 8 which presents a graph with a vertical axis for the percentage of the initial actuation force and a horizontal axis for the percentage of the actuation displacement. In the illustrated embodiment, the actuation force decreases slightly from the initial actuation force to the final actuation force during actuation of the button and compression of spring, due to an increase in mechanical advantage over the distance of travel. This is in contrast to traditional spring systems where the force generally increases linearly with increasing displacement during actuation.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A device for dispensing a medium, comprising:

an elongated body including a chamber for containing a medium and an outlet configured to deliver the medium through an oral or nasal opening; and a dispensing system for selectively placing the chamber in communication with the outlet, wherein the dispensing system includes a button that is selectively moveable in a direction transverse to the elongated body to actuate dispensing of the medium from the chamber through the outlet, wherein the dispensing system includes a conduit and a linkage operatively associated with the button, the conduit extending through the linkage and including a contoured portion to accommodate a path of the linkage, wherein the linkage is constructed to be displaced into the contoured portion of the conduit during actuation, and wherein a distance between an inlet and outlet of the conduit remains the same during actuation.

2. The device of claim 1, where the contoured portion of the conduit includes a deflection.

3. The device of claim 2, wherein the deflection is U-shaped and opens towards the path of the linkage.

4. The device of claim 1, wherein the linkage includes a pair of links joined at a moving pivot, the pivot moving transversely and axially in response to transverse movement of the button.

5. The device of claim 1, further including a valve operatively associated with the linkage, the valve being placed in and out of communication with the chamber in response to movement of the linkage.

6. The device of claim 5, further including an actuator slide moveable towards and away from the chamber in response to movement of the linkage, the actuator slide connecting the valve and the conduit in fluid communication.

7. The device of claim 1, further comprising one or more vents configured and arranged to draw ambient air into and through the elongated body to the outlet.

8. The device of claim 7, wherein the air is at least partially drawn in by a venturi effect of the medium flowing through the conduit.

9. The device of claim 1, wherein an end of the conduit proximate to the oulet of the elongated body is slidingly supported by a relief formed in the elongated body.

10. The device of claim 7, further comprising one or more channels connected to the one or more vents and extending toward the outlet, wherein the one or more channels are connected to the conduit.

11. A device for dispensing a medium, comprising:

an elongated chamber section for containing a medium;

an elongated dispensing section including an outlet configured to deliver the medium through an oral or nasal opening, a conduit in communication with the outlet, a valve, a button moveable in a direction transverse to the dispensing section, and a linkage operatively associated with the valve and the button, wherein the conduit extends through the linkage and includes a contoured portion to accommodate a path of the linkage, wherein the linkage is constructed to be displaced into the contoured portion of the conduit during actuation, and wherein a distance between an inlet and outlet of the conduit remains the same during actuation;

wherein the elongated chamber section and the elongated dispensing section are releasably attachable in end-to-end relation to form an elongated body, with the valve being opened in response to movement of the button in the transverse direction causing medium to flow from the chamber through the valve, along the conduit and out of the device via the outlet.

12. The device of claim 11, wherein the elongated dispensing section includes a first end, a second end, and a sidewall extending therebetween, and the button is moveable through an opening in the sidewall.

13. The device of claim 11, wherein the valve includes a valve stem having an end that is located in the chamber and an inlet opening located proximal of the valve stem end, the inlet opening being moveable into communication with the chamber in response to transverse movement of the button.

14. The device of claim 13, wherein an actuator slide is moveable towards and away from the chamber in response to movement of the linkage, the actuator slide connecting the valve stem and the conduit in fluid communication.

15. The device of claim 13 further including a spring located in the chamber that biases the valve stem away from the chamber.

16. The device of claim 11, wherein the contoured portion of the conduit includes a deflection.

17. The device of claim 16, wherein the deflection is U-shaped and opens towards the path of the linkage.

18. The device of claim 11, wherein the linkage includes a pair of first links and a pair of second links, with each of the pair of first links and the pair of second links are arranged on opposite sides of the dispensing section, each first link having a head that converges inwardly, and each second link having a tail that converges inwardly, the respective inwardly converging heads and tails forming a pivot junction between the pairs of first and second links.

19. The device of claim 11, further comprising one or more vents configured and arranged to draw ambient air into and through the elongated dispensing section to the outlet.

20. The device of claim 19, wherein the air is at least partially drawn in by a venturi effect of the medium flowing through the conduit.

21. The device of claim 19, further comprising one or more channels connected to the one or more vents and extending toward the outlet, wherein the one or more channels are connected to the conduit.

22. The device of claim 1, further comprising a valve stem associated with the chamber, wherein the valve stem and the conduit form a telescoping connection.

23. The device of claim 11, wherein the valve includes a valve stem, wherein the valve stem and the conduit form a telescoping connection.

24. The device of claim 11, wherein an end of the conduit proximate to the oulet of the elongated dispensing section is slidingly supported by a relief formed in the elongated dispensing section.

* * * * *